(12) United States Patent
Kahn et al.

(10) Patent No.: US 6,756,523 B1
(45) Date of Patent: *Jun. 29, 2004

(54) ADENOVIRUS VECTORS FOR THE TRANSFER OF FOREIGN GENES INTO CELLS OF THE CENTRAL NERVOUS SYSTEM PARTICULARLY IN BRAIN

(75) Inventors: Axel Kahn, Paris (FR); Gildas Le Gal La Salle, Saint Cloud (FR); Jacques Mallet, Paris (FR); Michel Perricaudet, Ecrosnes (FR); Marc Peschanski, Creteil (FR); Jean-Jacques Robert, Sceaux (FR)

(73) Assignee: Aventis Pharma S.A., Antony (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/460,478

(22) Filed: Jun. 2, 1995

Related U.S. Application Data

(63) Continuation of application No. 08/403,868, filed as application No. PCT/EP93/02519 on Sep. 17, 1993.

(30) Foreign Application Priority Data

Sep. 25, 1992 (EP) ............................................ 92/402644

(51) Int. Cl.⁷ ........................ A01K 67/00; A61K 48/00; C12N 5/10; C12N 15/861
(52) U.S. Cl. ............................ 800/9; 424/93.2; 514/44; 435/320.1; 435/325; 435/455; 435/456
(58) Field of Search ......................... 514/44; 536/23.72, 536/24.1, 24.2; 435/320.1, 235.1, 325, 455, 456; 424/93.21, 93.2; 800/9

(56) References Cited

U.S. PATENT DOCUMENTS

| | | | | |
|---|---|---|---|---|
| 4,920,209 A | * | 4/1990 | Davis | 435/235 |
| 5,501,979 A | * | 3/1996 | Geller et al. | 435/320.1 |
| 6,245,330 B1 | * | 6/2001 | Horellou et al. | 424/93.2 |

FOREIGN PATENT DOCUMENTS

| | | | |
|---|---|---|---|
| WO | 9005781 | * | 5/1990 |
| WO | 9104316 | * | 4/1991 |

OTHER PUBLICATIONS

Braithwaite, "Semipermissive replication of adenovirus 5 in rqt brain cells and evidence for an induction of cellular DNA replication in vivo", J. gen. Virol. 67: 391–396, 1986.*
Gluzman in Eukaryotic Viral Vectors, CSH, 1902, Oct. 20, 1997.*
Berkner in Current Topics in Microbiol & Immunol 158: 39, 1992, Oct. 20, 1997.*
Stratford–Perricaudet Human Gene Therapy 219: 51, 1991, Oct. 20, 1997.*
Rosenfeld Cell 68: 143, 1992, Oct. 20, 1997.*
Rojanasakul, Adv. Drug Del. Rev., 18:115–131, 1996.*
Friedmann, Trends in Genetics, 10(6) : 210–214, 1994.*
NIH "Report and Recommendations". . . Dec. 7, 1995, p. 1–40.*
Marshall, E., Science, vol. 269, Aug. 1995 pp. 1050–1055.*
Gutierrez et al, The Lancet, vol. 339, Mar. 1992 pp. 715–721.*
Neve, R., Trends Neurosci, 16 (7), Jul. 1993 pp. 251–3.*
Wang et al, Adv. Exp. Med. Biol., 309 B, (Purine Pyr. Metab. Man. 7) 1991, pp. 61–66.*
Culver et al, Science, vol. 256, Jun. 1992 pp. 1550–2.*
Rosenfeld et al, Science, vol. 252, 1991 pp. 431–4.*
Federoff et al, Proc. Nat. Acad. Sci. vol. 89, Mar. 1992 pp. 1636–1640.*
Oellig et al, J. of Neuroscience Res. vol. 26, 1990, pp. 390–396.*
Geller et al, TINS, vol. 14, No. 10, 1991 pp. 428–432.*
Shea et al, J. of Neuroscience Res., vol. 32; 1992 pp. 363–374.*
Watson, "Recombination at the Molecular Level", p. 313, Benjamin/Cumming Pub. Co. Inc., 1987.*
Cohen–Haguenal, Gene Therapy: Advances and Prospects, Pathologic et Biologie 40(1):5–13, 1992.
Babiss Friedman, Regulation of N–myc Gene Expression: Use of an Adeovirus Vector to, Molec. Cell Biol. 10(12): 6700–08, 1990.
Yang, Gene Transfer into Mammalian Somatic Cell In Vivo, Critical Reviews Biotech. 12(4): 335–56, 1992.
Irenaka, Nakahira, Nakajima, Fujimoto, Kagawa et al., Detection of Brain–Specific Gene Expression in Brain Cells in Primary Culture, New Biologist 4(1): 53–60, 1992.
Gage, Rosenberg, Wolff, Friedman, Grafting Genetically Modified Cells to Treat Diseases of the Central Nervous System., WO 90/06757 Dec. 12, 1989, Jun. 28, 1990.
Preston Ace, Herpes Simplex Virus Type 1 Mutant, WO 91/02788 Aug. 14, 1990, Mar. 7, 1991.
Geller, During, Wilcox, Federoff, Pardee et al., Cell Type Specific Alteration of Levels of Gene Products in Neural Cells, WO 92/07945 Oct 23, 1991, May 14, 1992.

* cited by examiner

*Primary Examiner*—Scott D. Priebe
(74) *Attorney, Agent, or Firm*—Finnegan, Henderson, Farabow, Garrett, & Dunner LLP

(57) ABSTRACT

The invention concerns a recombinant DNA vector characterized in that it is capable of directing the expression an/or transcription of a selected nucleotide sequence in the cells of the central nervous system and in that it comprises (i) at least part of the genome of an adenovirus, including the regions required for that adenovirus to penetrate into the cells normally infectable by that adenovirus and (ii) being inserted into said part of genome of an adenovirus under the control of a promoter, either present or also inserted into said genome part and operative in said cells. This recombinant vector finds particular use in the treatment of diseases of the central nervous system, also in gene therapy.

108 Claims, 8 Drawing Sheets

ADENOVIRUS VECTORS FOR THE TRANSFER OF FOREIGN GENES INTO CELLS OF THE CENTRAL NERVOUS SYSTEM PARTICULARLY IN BRAIN

This application is a continuation of application Ser. No. 08/403,868, filed Apr. 28, 1995, as a 371 of PCT/EP93/02519, filed Sep. 17, 1993, which claims priority to EP 92/402644.6, filed on Sep. 25, 1992.

To transfer safely and efficiently therapeutic DNA into the central nervous system, is a formidable challenge in the development of active therapies in brain diseases.

Preliminary investigations have been carried out with a number of vectors, more particularly retroviral vectors and herpes simplex derived vectors. However the usefulness of such gene transfer vehicles has, to date, been limited.

In most cases, retroviral vectors are not useful because they are unable to infect postmitotic cells, including most neural cells (1). Herpes simplex derived vectors infect neural cells but problems of pathogenicity and of stability of gene expression remain unsolved (2,3). In addition Herpes simplex derived vectors have so far proven to have but limited efficacy of expression. In a most recent article (4) the authors refer to the short-term expression reported earlier of HSV-1 derived vectors, because most of the promoters used had only been active during the acute phase of viral infection (less than 10 days post-infection). They disclosed the expression of a b-glucuronidase gene in a cell of the central nervous system under the control of the LAT promoter normally associated with the latency-associated-transcript (LAT) sequence of the virus. But the authors also report that, even though their experiments demonstrated the feasibility of using the LAT promoter for long-term expression of foreign genes in cells of the central nervous system to correct a genetic enzymatic deficiency in infected cells, too few cells had been corrected to alter the disease phenotype. Consequently their vector system needed to be improved to correct sufficient cells for obtaining a clinically significant effect.

The invention aims at obviating such difficulties and at providing most effective vector systems capable of delivering foreign genes and, where appropriate, their transcription products or expression products directly to cells of the central nervous system, particularly to terminally differentiated cells, incapable of proliferation. A more particular object of the invention is also to allow for the wide spreading of such vector systems throughout the neural tissue to be infected, yet while remaining substantially confined thereto.

Still another object of the invention is to produce such vector systems which are sufficiently safe to allow for a study and regulation in vitro of cloned genes in such cells or in test animals, and for therapy, in man or animal, involving the in situ production of a selected expression product, including gene therapy.

The invention is based on the recognition that adenovirus-derived vectors, particularly non-replicative adenovirus vectors, are capable of fulfilling these aims, both in vitro and in vivo. They provide powerful delivery systems of genes into the cells of the central nervous system, more particularly brain cells. They are characterized by a degree of infectivity of sufficient magnitude to allow for the infection of considerable populations of cells. The biological experiments disclosed hereafter demonstrate the capability of adenovirus derived vectors (or adenoviral vectors) of efficiently infecting nerve cells, particularly neurons, both in vitro and in vivo.

Thus the invention provides a process for the production of a recombinant vector useful in a method comprising causing the transcription product or the expression product of a nucleotide sequence coding for a selected polypeptide to be targeted or produced in cells of the central nervous system, e.g. brain cells, particularly neural, glial or ependymal cells, wherein said recombinant vector is an adenoviral vector which comprises at least part of the genome of an adenovirus including those regions of that genome which provide the genetic information required by that adenovirus to penetrate into cells normally infectable by it, said nucleotide sequence being inserted in said genome part, under the control of a promoter either present or also inserted within said adenoviral vector, and said promoter being operative in said cells.

Thus the invention is more particularly related to the use of an adenovirus-derived vector for the expression of a selected nucleotide in the cells of the central nervous system.

The invention also provides a recombinant DNA vector characterized in that it is capable of directing the expression and/or transcription of a selected nucleotide sequence in the cells of the central nervous system and in that it comprises (i) at least part of the genome of an adenovirus, including the regions required for that adenovirus to penetrate into the cells of the central nervous system, and (ii) said selected nucleotide sequence under the control of a promoter operative in said cells.

Figure 1:
FIG. 1 shows morphological and anatomical characteristics of neurons in the hippocampus.

The powerful capability of adenoviral vectors of transferring gene fragments in vivo into quiescent neural cells is illustrated by the experiments reported hereafter, which were carried out with an adenovirus vector carrying the E. Coli lac Z gene or the human tyrosine hydroxylase gene, in neural cells of adult rats. A large number of neural cells (including neurons, astrocytes, microglia and ependymal cells) expressed these transgenes at least 60 days after inoculation of various brain areas. Injecting up to $3 \times 10^5$ pfu in 10 $\mu$l did not result in any detectable cytopathic effects, which were only observed for the highest titers of infection ($<10^7$ pfu/10 $\mu$l) and were most likely associated with a massive endocytosis of viral particles in neural cells close to the injection site.

Moreover the genomes of adenoviruses can be manipulated to accommodate foreign genes of 7.5 kb in length or more. It has a large host range, a low pathogenicity in man, and high titers of the virus can be obtained (5).

It will be readily appreciated that these results strongly support the presumption that adenovirus offers, as a vector, a new and remarkable tool to genetically modify quiescent cells of the nervous system, because of its great efficacy of infection, long term expression, wide host range and low toxicity. Thus, adenovirus should be instrumental in the study of the function of cloned gene products in their physiological and anatomical context. The ability to infect the hippocampus (as this will be shown later) is of great interest to study integrated phenomena such as long-term potentiation, in animals.

Moreover the adenovirus clearly appears as an efficient means to transfer foreign genes into the brain with a therapeutic goal. Adenovirus vectors have great potential for gene therapy of nervous system diseases, such as the local delivery of growth factors or neurotransmitters for degenerative diseases and, more generally, to replace defective genes in appropriate cells. Relatively low titers of adenovirus vectors can efficiently transfer foreign genes into a significant number of brain cells without triggering pathological effects. Subject to optimization of the doses of recombinant adenoviral vectors containing a foreign gene to be delivered into brain cells, they open new avenues in the treatment of many genetic and acquired neurological diseases, consequently, an alternative to drug treatment or brain transplantation of fetal tissues.

Adenoviruses, particularly adenoviruses of type 2 or 5 (Ad2 or Ad5) are particularly preferred. They are relatively stable, can be cultured easily and rapidly (viral cycle of about 30 hours) and provide high titers: up to $10^4$–$10^5$ plaque forming units (p.f.u.) per infected cell. They are not oncogenic. The complete sequence of their viral genome has been established (6) and its molecular biology has been studied extensively. Finally several mutants, particularly deletion mutants, have been obtained, which makes it possible to insert fragments of large size therein (7).

Preferably the recombinant vectors for use in this invention are defective adenoviruses, whose genomes no longer contain those nucleotides sequences required for the virus replication in cells (other than brain cells) normally infectable by it. More particularly, they are free of the E1 region, including the early E1a region which activates the other early trancription units of the virus required for its replication as well as the region E1b involved in the establishment of a fully transformed phenotype, in the protection of DNA sequences during viral infection and required for the normal progression of viral events late in infection.

Preferably too, they are devoid of the E3 region which is involved in cellular immunity in vivo and is totally dispensible for growth in vitro.

Preferably however the recombinant vector for use in that invention comprises all of the sequences that are essential for the adenovirus encapsidation.

The promoter controlling the sequence coding for the selected polypeptide to be targeted or produced in the cells of the central nervous system, can either be endogenous or exogenous with respect to the adenoviral parts of the recombinant vector.

A preferred homologous promoter is any one that is likely to be recognized by the polymerases, practically RNA polymerase II, of human or animal cells infected by such adenoviruses. A particularly preferred endogenous promoter is the major late strong promoter (MLP) of the human adenovirus of type 2 (Levrero et al., 1991) (8). Another promoter that may be used consists of the early promoter of the E1a region of the adenovirus. In that last instance, a preferred defective adenovirus is devoid of its 5' region normally upstream for that early promoter. In that last instance, the nucleotide sequence sought to be introduced in the neural cells is substituted for the E1A region.

The endogenous promoters of the adenoviruses can also be replaced by other ubiquitary promoters of heterologous or exogenous origin, e.g.:

a promoter contained in the LTR (Long Terminal Repeat) of the Rous Sarcoma Virus (RSV) or the LAT promoter referred to above, a promoter of the IE gene of Cytomegalovirus (CMV), inducible MMTV promoters (originating from the mouse mammary tumor virus) or metallothionine promoters.

Other promoters can be used too. Particularly, ependymal, neural or glial promoters will be preferred, particularly in instances where the nucleotide sequence inserted in the adenoviral vector is to be targeted more specifically on more specific classes of neural cells. Reference is for instance made to the following promoters, particularly those involved in the genes coding for neurotransmitter synthesizing enzymes:

TH (tyrosine hydroxylase)

CHAT (choline acetyl transferase)

TPH (tryptophane hydroxylase)

GFAP (glial fibrillary acidic protein) enolase g (neuronal protein marker)

aldolase C.

The invention relates also to a process for making such recombinant vectors, which process comprises inserting the nucleotide sequence whose expression is sought in the starting vectors and the transformation of infectable cells with said vectors. Where the vector is a full live virus, the recombinant viruses are then recovered from the cell culture medium. Where the recombinant vector is a defective virus, a preferred process then comprises the transformation of a transformable eucaryotic cell line (preferably of human or animal origin) which itself comprises a distinct nucleotide sequence capable of complementing the part of the adenovirus genome that is essential for its replication and which is not present in said vector, whereby that complementation sequence is preferably incorporated into the genome of said cell line.

By way of preferred examples of such cell lines, one should mention the so called "293 cell line" derived from human embryonary kidney which contains, integrated in its genome, the first 11% of the 5' region of an Ad5 virus genome. That portion of the Ad5 genome enables recombinant viruses defective in that region, because of a deletion of part that region, to be appropriately complemented. Such a process for the production of defective viruses has been described more particularly in European patent application n° EP 185573, filed on Nov. 20, 1985.

After transformation of such cell lines, the defective recombinant viruses are multiplied, recovered and purified.

Needless to say that the same process may be applicable to the production of other defective adenoviruses as a result of a deletion in a region other than in the 5' region referred to hereabove, it being then understood that the cell lines used in such production should then include in their own genome the sequence deleted form the adenoviral genome to thereby allow for the complementation of such defective adenoviruses.

The invention provides thus for the first time a serious alternative to injection in the brain area of cells, e.g. embryonic cells carrying the relevant genetic information, in gene therapy aiming at correcting metabolic deficiencies or defects in the targeted cells, particularly post-mitotic neurons. This is the consequence of the important infective power of adenoviruses, also retained by the corresponding defective adenovirus-derived vectors, of their capacity of spreading throughout the targeted neural or nerve tissue while also remaining substantially confined within the selected tissue, if specifically injected thereinto, as well as of the long-term transcription, and in most instances, expression of the nucleotide sequence carried into the nerve tissue by such adenoviral vectors.

The nucleotide sequence whose introduction in the cells of the central nervous system may be sought, may consist of any sequence capable of providing molecules interacting with the metabolism of such cells. Such molecules may consist of selected anti-sense RNAs, or anti-sense oligoribonucleotide, capable of interacting with defective messenger RNAs whose further processing, responsible for corresponding diseases, ought to be blocked, e.g. in a number of neuropsychiatric diseases, epilepsy, etc . . . This methodology appears of particular interest in the treatment of the Alzheimer's disease. The anti-sense method could be used, by way of example only, for inducing a blockade of the b-amyloid precursor, for preventing an accumulation of the b-amyloid peptide in the senile plaques. Alternatively use could be made of anti-sense oligonucleotide capable of inhibiting the expression of enzymes involved in the abnormal phosphorylation of proteins, e.g. the TAU protein involved in Alzheimer's disease. Alternatively again the nucleotide sequence is one which could sequester specific binding proteins, themselves normally involved in the processing of the DNA or RNA sequence whose transcription or expression is sought to be inhibited.

The nucleotide sequence whose introduction in the cells of the central nervous system may be sought, may also code for an expression product having a biological property. Said expression product may for example be capable (1) of compensating a corresponding defective natural polypeptide containing product encoded by a defective corresponding nucleotide sequence, or (2) of compensating the lack of endogenous production of the natural endogenous corresponding polypeptide containing product in said targeted cells, or (3) of introducing new therapeutic activities in the infected cells. Examples of such defective polypeptide-containing products may consist of neurotransmitter-synthesizing enzymes and growth factors. For example in the case of Parkinson's disease (which is characterized by a vulnerability of dopaminergic cells) one could envisage producing locally DOPA or dopamine by expressing the cDNA encoding tyrosine hydroxylase, or a growth factor such as BDNF (brain derived neurotrophic factor) which could favor the survival of dopaminergic neurons. Likewise for Alzleimer's disease, where one of the missing neurotransmitters is acetylcholine which is synthesized by choline acetyl transferase. Moreover NGF (nerve growth factor) could prevent degeneration of cholinergic neurons.

Another potentially useful factor to express is CNTF (ciliary neurotrophic factor) which could prevent neuron death. But CNTF may also have interesting effect in the brain, e.g. for the blocking of the destruction (seemingly induced in diabetes affected patients) of peripheral nerves. Other trophic factors whose expression may be sought consist, by way of examples of IGF, GMF, aFGF, bFGF, NT3 and NT5.

In a general manner growth factors could be caused to be produced in neuronal cells of patients affected with neuropathies, strokes, spinal cord injury, amyotrophic lateral sclerosis, Huntington's chorea, Azeimer's and Parkinson's diseases, cerebral palsy. Epilepsia may be, among other possibilities, treated by a local production, in the central nervous system, of the neurotransmitter GABA, as a result of the expression of the glutamic acid decarboxylase.

The invention is also of particular interest for the preparation of compositions for use in the treatment of hereditary diseases affecting the defective or deficient product of the mutant gene: lysosomal enzymes in lysosomal diseases (e.g. hexosaminidases in Tay Sachs and Sandhoff diseases, aryl-sulfatase in metachromatic leucodystrophy, glucocerebrosidase in Gaucher's disease, b-glucursoronidase in mucopolysaccharidosis, HGPRT in Lesh Nyhan disease, etc . . . ). Hereditary progressive neuron degenerations could be treated by transfer of the normal disease gene via adenoviral vectors, or, as discussed above, by induction of a local production of growth factors. For instance, it has been shown, that production of CNTF could slow down progressive motoneuronal degeneration (pmm) of mice (Sendtner et al, Nature 1992;358: 502–504), the same being observed with aFGF on photoreceptor degeneration in inherited retinal dystrophy in rat (Faktorovich et al, Nature 1990; 347:83–86). Acquired spinal cord diseases like the frequent and constantly lethal Amyotrophic Lateral Sclerosis (ALS) could perhaps benefit from similar local production of CNTF that has been proved to protect motoneurons.

Inherited dysmyelinating diseases could also be improved by adenovirus-mediated gene transfer into myelin-synthesizing cells.

Finally, some other types of potential therapeutic agents could be locally produced into the CNS, for instance enkephalins to attenuate rebel pains, for instance in cancerous patients.

The invention also relates to the pharmaceutical compositions consisting of the recombinant adenoviral vectors containing the nucleotide sequences as defined above, in association with a pharmaceutical carrier suitable for the administration route to be selected, e.g. direct in situ injection of the viral suspensions obtained in the relevant neural tissue (or though far less preferred, through a general route, e.g. intravenous route, particularly when the adenoviral vector also contains a promoter selectively operative in determined nerve tissue or cells).

The invention is not limited to the therapeutical uses contemplated hereabove, of the adenoviral vectors. The latter can also, owing to their high infectivity, be used either in in vitro assays on determined populations of neural cells, e.g. for the sake of studying the capacity of a promoter (then coupled to a suitable "marker", e.g. b-gal) of being recognized by the polymerases of said neural cells. Alternatively such adenoviral vectors can also be used for the detection or the evaluation of the interaction recombinant virus (that expressed by the nucleotide sequence under the control of a promoter operative in such cells) with a given population of neural cells or a more complex nerve tissue. For instance that evaluation or detection may aim at localizing those cells of the more complex tissue which carry a receptor for the virus. The detection can make use of any appropriate classical labeled method, e.g. use of labeled antibodies to detect expression products of the nucleotide sequence assayed. The prospects of these evaluations may be considerable in the field of neuroanatomy.

The recombinant vector of this invention is also useful in a method comprising causing the transcription product or expression product of a nucleotide sequence coding for a selected polypeptide to be targeted or produced in cells of the central nervous system, e.g. brain and spinal cord cells, particularly neural, glial or ependymal cells, of an animal and detecting the resulting physiological or behavioral modification induced in said animal by said transcription product or said expression product.

For instance in the case of a lesion of the septohippocampic track which depletes the hippocampus in acetylcholine, it would be possible to study the effects of the transfer of a gene coding for the choline acetyl transferase (ChAT) in the hippocampus. The introduction of that gene in the target core of cholinergic fibers (cut by the lesion) could elicit a re-increase of the amount of the available acetyl choline and, consequently, correct the deficit. This deficit can be evaluated by behavioral tests of memorization. For instance mice thrown in a "swimming pool" can learn to find again a platform which enables them to escape to water (Morris swimming pool). However the animals whose septo-hippocampic track has been deteriorated are very handicapped in that operation. The detection of an increase of the acetyl choline produced as a result of the gene expression would then be appreciated by the ease with which the animals would be able again to find the platform.

According to another example, the invention would enable the analysis of the degree of compensation of troubles of the motor behavior produced by the denervation of the striatum, particularly in the event of a lesion of the dopaminergic cores of the mesencephale (substance nigra). The introduction of the gene coding for tyrosine hydroxylase (TH) in the striatum could correct that deficit. The compensation can be evaluated by the study of the behavior of rats in the rotation test: animals wounded on one side only rotate in a repetitive fashion (over ten rotations per minute) when they receive an injection of apomorphine. The production of dopamine (linked to the introduction of the TH gene) could be appreciated in that behavioral test.

Still according to another example, the invention allows for the electrophysiological and behavioral study in other cases. For instance, the neurones of the dorsal horn of the spinal cord which transmit information bound to nociceptive stimulation (pain channels) are sensitive to morphine which causes their activity to be decreased. The introduction of a gene coding for an endomorphine in the spinal cord could provoke a secretion of this substance which, like morphine, would act of these cells. Such an action could be evaluated by behavioral tests (threshold of reaction of animals to nociceptive stimulation) as well as by electrophysiological studies on the neurones themselves of the spinal cord. Recording of the activity of these cells would enable one to appreciate the existence of a modulation induced by the expression of the transferred gene.

The possibilities afforded by the invention will be further illustrated, yet in a non-limitative manner by the description of a number of assays, which are in part supported by figures appended to the present description. Particularly, the Ad.RSVbgal appears as an appealing means to analyze neuronal and glialmorphology in specific areas of the brain by providing Golgi-like staing of cells at the injection site. Filing up of the axons by the enzyme may additionally provide ways to analyze projections of discrete neuronal populations. Conversely uptake of the virus by the terminals and subsequent retrograde transport to the neuronal cell body allows tracing of sets of afferents to a specific brain area.

One major advantage of this technique for neuroanatomy is the easy combination of the X-gal stain with all sorts of other labeling techniques, in particular immunocytochemistry. The use of vectors in which the nls sequence would be omitted might improve the efficacy of such a technique.

Similarly that adenoviral vector provides a basis for the study of the action of other promoters substituted for the RSV LTR promoter, with respect to different neural cell populations.

Assays 1

Use has been made of the replication defective adenovirus, the Ad.RSVbgal, which expresses a nuclearly targeted b-galactosidase (b-gal) driven by the Rous sarcoma virus long terminal repeat (RSV LTR) promoter (9). The SV40 nls (nuclear localization signal) in said vector provided for the targeting of the vector to the nuclei of the cells. The ability of this vector to infect primary cultures of sympathetic neurons of superior cervical ganglia (SCG) and astrocytes was tested. The b-gal activity was visualized histochemically using the chromogenic substrate 5-bromo4-chloro-3-indolyl-b-D-galactosidase (X-gal) (10). SCG cultured in the presence of an antimitotic agent provide a convenient means to obtain a pure and homogeneous preparation of neurons (11).

More particularly expression of b-gal in cultured sympathetic neurons and astrocytes after inoculation by adenovirus Ad.RSVb-gal was carried out as follows:

SCG were removed from 2 day-old Wistar rats, dissociated, plated onto 16 mm collagencoated dishes and cultured as described in (11). Cytosine arabinofuranoside (10 $\mu$M) was added during the first week of culture to prevent proliferation of ganglionic non-neuronal cells. After 6 days in the culture, cells were inoculated with $10^6$ plaque-forming units (pfu) of Ad.RSVbgal in culture medium or, as a control, exposed only to culture medium. Twenty-four hours later, the virus was removed and cells were maintained for 2 days in culture medium. Cells were washed, fixed with paraformaldehyde and b-gal activity was then revealed by histochemical staining (10).

After 6 days of culture the following observations were made: virtually all cells were b-gal positive, with no apparent toxic effects or morphological changes. Positively labeled cells could not be detected when the staining reaction was performed in a parallel non-inoculated culture.

The ability of adenovirus to infect primary cultures of rat hippocampal tissue enriched in astrocytes was tested too. Inoculation resulted in a blue nuclear staining in about two-thirds of the cells. The identification of b-gal positive cells as astrocytes was confirmed by additional staining with an antibody against glial fibriliary acidic protein (GFAP).

More particularly the assays were carried out as follows. Primary enriched astrocyte cultures were established from neonatal rat hippocampal tissue as described elsewhere (12). Cells were plated in 35 mm diameter plastic dishes and grown in supplemented Dubelcco modified Eagle's medium (DMEM) for 5 days. 2 $\mu$l of the adenoviral solution (titer $10^8$ pfu/ml) were then inoculated in each dish for 24 hours. After washing and paraformaldehyde fixation, cells expressing b-gal were characterized using X-gal histochemistry. A superposition of the two labels was observed (not represented).

Assays 2

The feasibility of adenovirus to infect brain cells in vivo was evaluated in number of characteristic structures.

Seventeen male Wiatar rats (10 week-old) were stereotactically injected under deep anesthesia with 1 to 5 $\mu$l of media containing $10^{10}$ plaque-forming units (pfu)/ml of highly purified virus into either the hippocampus or the substantia nigra. Animals were sacrificed at 1, 2, 3, 5, 7, 30 and 60 days after inoculation. b-gal activity in positive cells was detected histochemically by using both the X-gal substrate, and an antibody directed against the protein (antibody was an affinity-purified rabbit IgG fraction to b-gal (Cappel, 1:800 dilution) which was then bound with a streptavidin-biotinylated peroxidase complex (Amersham) with diamino-benzidine as a chromogen, reinforced with nickel). The latter method is more sensitive and in some instances revealed b-gal in fine cytoplasmic processes due to high expression of the transferred gene.

All injected animals displayed a high level of b-gal activity. The expression was detected as early as 24 hours after inoculation and persisted in animals analyzed after two months. The diffusion of the virus was greater in the hippocampus than in the substantia and it spread through the entire dorsal hippocampus. In the substantia nigra, the overall pattern of infection was more restricted and distributed along a medio-lateral orientation. This difference may likely reflect the propensity of the virus to spread through tissues with a low adhesivity, such as the hippocampal fissure and the boundaries between the granule cell layer of the dentate gyrus and surrounding tissues.

In the hippocampus, the extent of the infected area was correlated with the volume of viral solution administered. Typically, in rats sacrificed 3 to 7 days after hippocampal inoculation, the infected area ranged from 1 to 4 mm3 for 3–5 $\mu$l injected virus ($10^{10}$ pfu/ml). Interestingly, a careful examination of the hippocampal sections over time, revealed a change in the pattern of labeling. While only minor differences were noticed within the first week post inoculation, a remarkable remodeling in the distribution of labeled cells was observed after one month. This new pattern was maintained after two months. In this long-term pattern, the distribution of b-gal positive cells was less diffuse, the labeling appeared to be confined to a defined cell layer.

No apparent cytotoxic effect was observed in the infected animals. All survived the inoculation without any noticeable behavioral abnormalities. Examination of the virus-infected brains revealed no enlargement of the lateral ventricle, nor disruption of the normal cytoarchitecture of the structures. The only noticeable alteration was a local tissue necrosis and reactive gliosis, which was restricted to the injected site. This phenomenon was largely due to the injection itself since a similar effect was observed in animals injected with saline. Finally, analysis of hippocampal sections at a cellular level with Nissl staining showed no cell loss nor evidence of cytolysis within the pyramidal cell layers or the granule cell layer of the dentate gyrus.

Assays 3

The preceding results establish that the adenovirus can infect brain cells. The following experiment establishes more particularly that neurons can be infected in vivo.

Glial and neuronal cell types were infected by direct in vivo inoculation of the adenovirus Ad.RSVb-gal. The b-gal expression in microglial cells was made by immunohistochemical detection near the injected area of a rat which received intrahippocampal injection 5 days before sacrifice. Immunohistochemical reaction was processed using peroxidase reinforced with nickel and with fluorescein conjugated secondary antibody.

Shortly after injection many of the b-gal positive cells exhibited a morphology typical of microglial cells. These small cells display fine, highly branched processes extending radially away from the cell body. Although microglial cells represented a large proportion of b-gal expressing cells up to one week, their numbers decreased drastically at longer post-infection times. Other infected cells detected during the early time points were demonstrated to be astrocytes by double staining using the X-gal substrate and an antibody directed against the astroglial glial fibrillary acidic protein (GFAP) (data not shown).

Compelling evidence that some of the infected cells are neurons was established for both injected cerebral structures. In the case of the substantia nigra, the presence of b-gal in dopaminergic cells could be documented using an antibody directed against tyrosine hydroxylase (TH), a classical marker of catecholaminergic neurons. Higher magnification clearly revealed that cells marked with TH antibodies also exhibited a blue nucleus. These cells account for about 50% of the b-gal positive cells within the infected dopaminergic cell area. In the hippocampus, numerous labelled cells were unambiguously identified as neurons based on both morphological and anatomical characteristics (FIG. 1). In some cells, the staing revealed a Golgi-like profile due to the diffusion of b-gal, resulting from high level of expression of the enzyme. This pattern was observed mostly from 48 hours to one week. Pyramidal neurons, granule cells and hilar interneurons were seen in the pyramidal cell layer CA1, the granule cell layer and the hilus of the dentate gyrus. These latter cells could easily be identified because of the characteristic cytoarchitecture of the hippocampus which is composed of distinctly segregated and laminated cellular subgroups. Occasionally, long stained processes were observed at distances greater than 400 $\mu$m from the cell body, confirming the neuronal nature of these cells. In addition, several segments with giant varicosities were seen running through the hilus, indicating that mossy fibers were also labelled.

Figure 2:
FIG. 2 shows b-gal positive cells in the left dentate gyrus of a hippocampus from a rat inoculated with Ad. RSVb-gal adenovirus.
Figure 3:
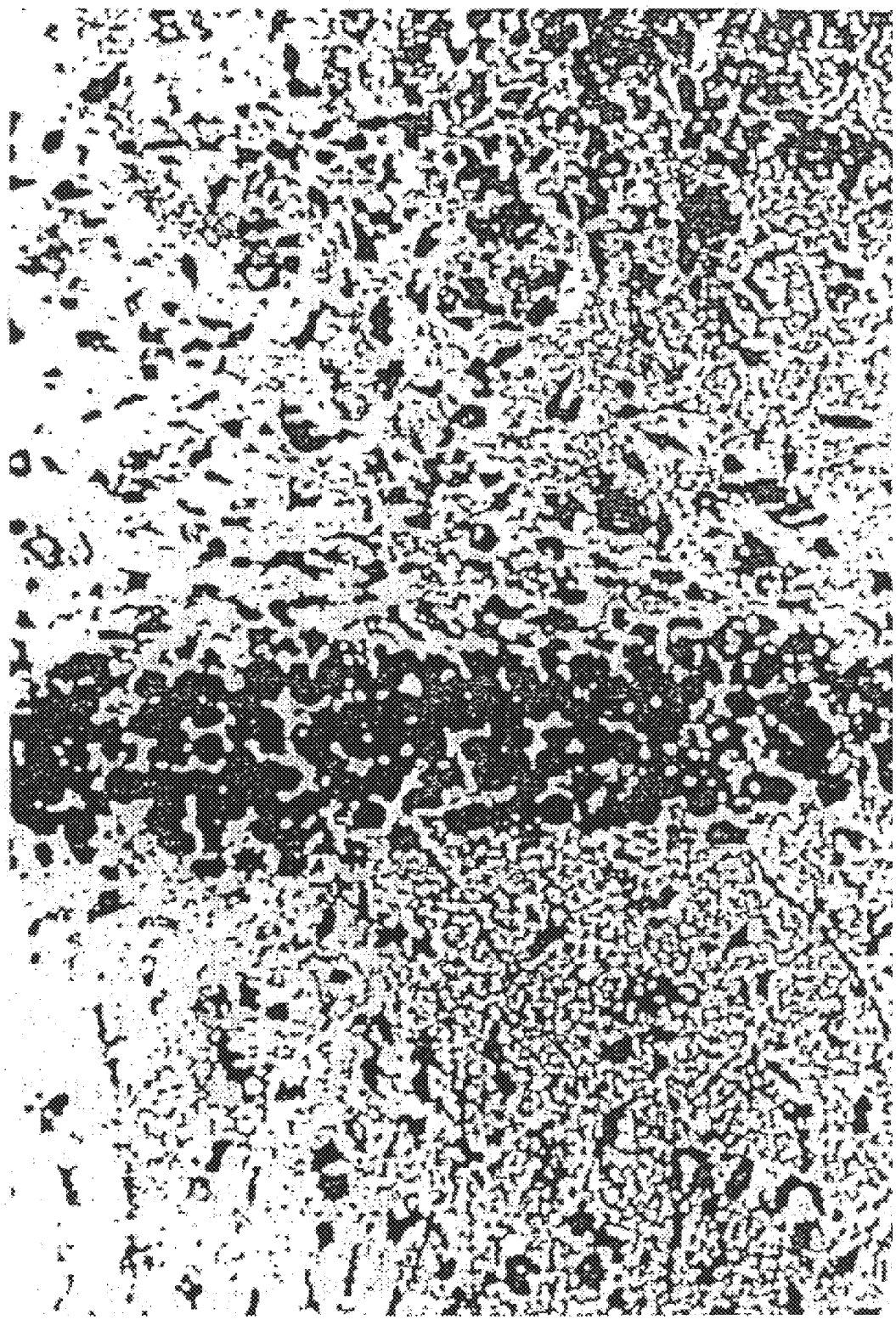
FIG. 3 shows densely packed b-gal labeled cell nuclei in the granule cell layer of the dentate gyrus.

As pointed out above, in all the rats sacrificed at one or two months after inoculation, the distribution and number of positive b-gal cells are markedly different from that observed at earlier time points. The distribution of b-gal positive cells was evaluated in the dentate gyrus one month after Ad. RSVb-gal adenoviral inoculation, using X-gal histochemistry. The blue labeled cells were found to be concentrated in the left dentate gyrus of the injected hippocampus, as compared to non-injected contralateral side (FIG. 2 Scale bar, 1 mm). Dentate localization of infected cells was confirmed by immunohistochemical b-gal detection (staining using peroxidase plus nickel). A high magnification (40x) view shows the great number and densely packed b-gal labeled cell nuclei in the granule cell layer of the dentate gyrus (FIG. 3 Scale bar, 300 $\mu$m).

The molecular layer, which was highly infected at shorter post-inoculation times, was then devoid of stained cells. As detected in sections counterstained with cresyl violet (data not shown), b-gal positive cells coincided with that of the granular layer and no positive cells were seen in the innermost part of the layer which includes most of the basket cells and a few glial cells. The blue staining in the rat sacrificed after two months was exclusively concentrated in the granule cell layer.

Assays 4

The high level of neural cell infectability by the adenovirus is further demonstrated by the results of the experiments reported hereafter.

Methods:

Adenovirus vectors containing the LacZ gene were prepared according to procedures described previously (5). Thirteen adult Sprague-Dawley rats (Charles River France) were anesthetized using chloral hydrate (400 mg/kg, i.p.) and placed in a stereotactic apparatus. A viral suspension containing $3.3 \times 10^{10}$ to $10^{11}$ plaque forming units (pfu) per ml was injected over ten minutes using a Hamilton syringe (10 μl, total injection: $3.3 \times 10^8$ to $10^9$ pfu) into the XIIth nucleus (n=6) or into various regions of the forebrain (n=7). After four days survival time, rats were reanesthetized and perfused transcardially with 4% paraformaldehyde in phosphate buffer (0.1 M; pH 7.4). The central nervous system was removed, post-fixed for 4 hours then cryoprotected overnight in 30% sucrose. Parasagittal sections (48 μm-thickness) were cut on a cryostat. Every fourth section was incubated for 4 to 12 hours at 28–30° C. with the X-gal stain as described previously (10). In three rats, X-gal treated sections were rinsed in phosphate buffer then further treated using classical immunohistrohemical techniques with Vectasin kits (Vector labs) using either a rabbit polyclonal antibody raised against GFAP (1/500) or the mouse monoclonal antibody OX42 (1/1200) that specifically stains microglial cells in the rat central nervous system. Sections were then mounted on gelatinize slides and every other section was counterstained with cresyl violet before final coverslipping from toluene.

FIG. 4 provides photomicrographs showing b-galactosidase histo-chemical staning in various cell populations in the rat brain after the above said adenovirus injection a. and b. labeling observed after injection into the nucleus of the twelfth nerve (XII). Virtually all the neurons in the XII nucleus have been infected, staining extending in all neuronal processes including axons (arrow in a.), providing a "Golgi-like" appearance of the cells. Some of the infected cells can be identified as astrocytes (arrowheads) by the brown reaction product indicating immunoreactivity for GFAP (glial fibrillary acidic protein). d., Staining in ependymal cells (ep) following a intra-ventricular injection. Sections in a, b and d have been counterstained with cresyl violet.

The following observations were made.

Figure 4A:
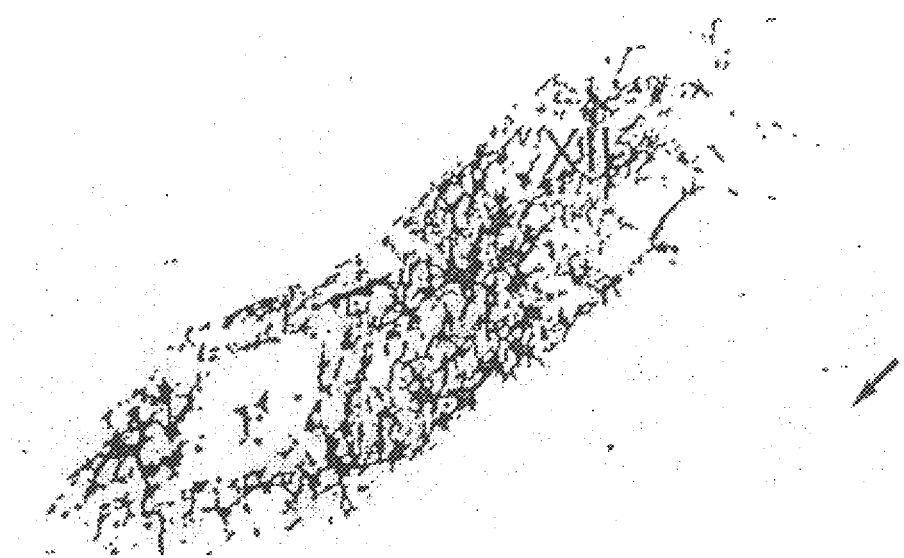
FIG. 4a shows labeling of neurons observed after injection of adenovirus into the nucleus of the twelfth nerve.
Figure 4B:
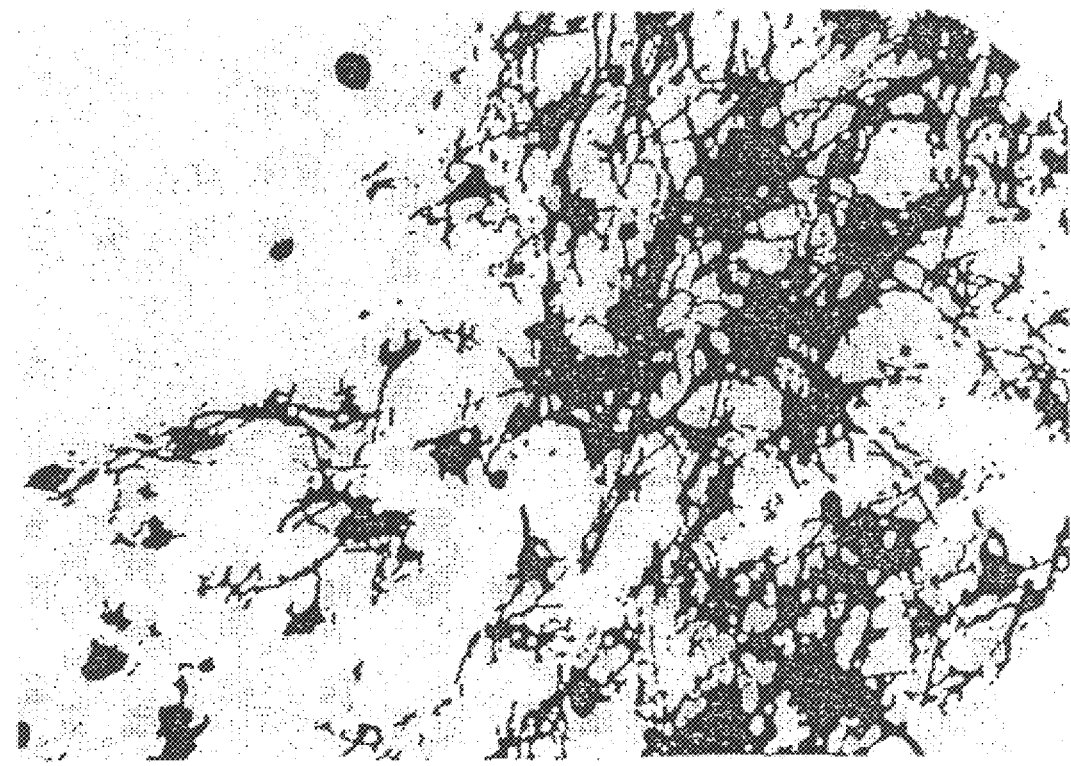
FIG. 4b shows labeling of neurons observed after injection of adenovirus into the nucleus of the twelfth nerve.
Figure 4C:
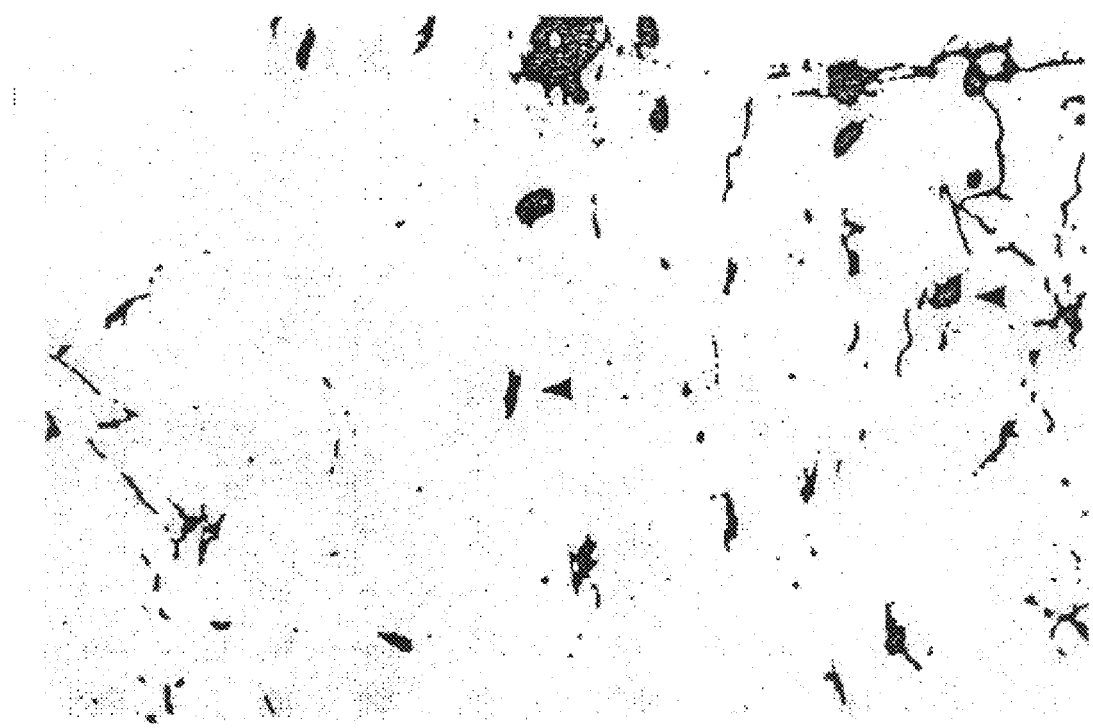
FIG. 4c shows b-gal histochemical staining of astrocytes after injection of adenovirus.
Figure 4D:
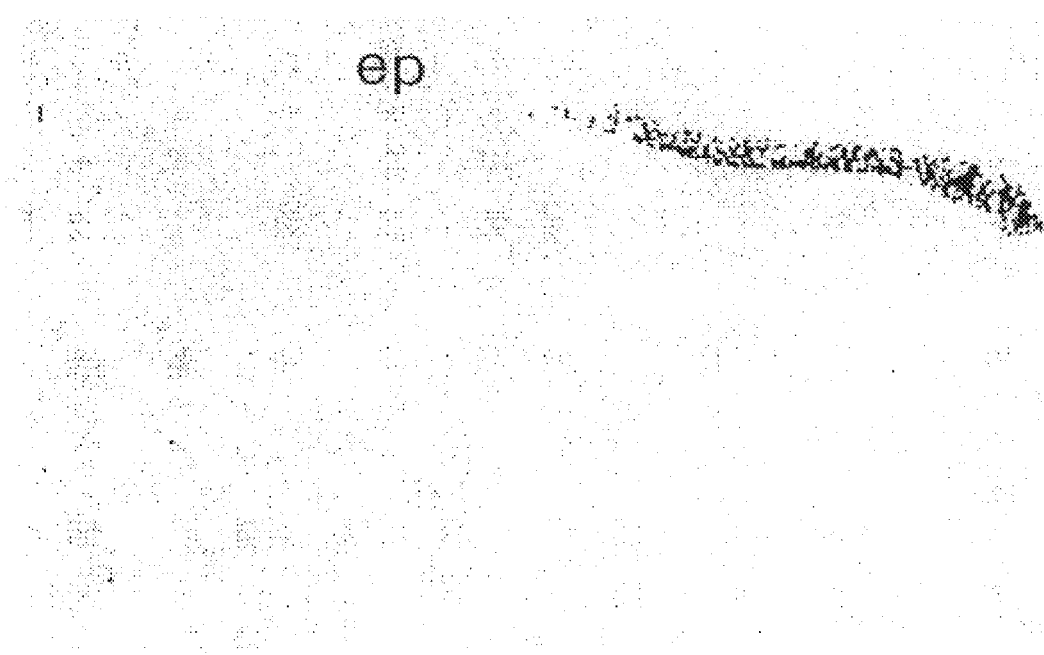
FIG. 4d shows b-gal histochemical staining of ependymal cells after injection of adenovirus.

No gross adverse effect of this inoculation on the animals' health and behavior was observed up to 60 days after inoculation (the longest time studied). In all cases, a large number of cells were histochemically stained. Neural cells were infected including neurons (FIGS. 4a,b) and glia identified as astrocytes (FIG. 4c) or microglia (not shown) in double-staining experiments using specific immunocytochemical markers. When injections were aimed at the ventricular system, a wealth of ependymal cells expressed the gene (FIG. 4d).

In the brain parenchyma, labeled cells were mostly found within 500 to 1000 μm from the needle track. Borders of the area containing infected cells tended to respect anatomical boundaries such as large fiber tracts or lamellae. For example, injections aimed at the nucleus of the XIIth nerve (FIG. 4a,b) produced virtually a complete and intense staining of all neurons within the nucleus while surrounding areas contained only scattered infected cells. Similarly, injected ependymal cells were observed over several millimeters after intraventricular injections, while adjoining neural tissue did not contain any stained cells (FIG. 4d). It is likely, therefore, that the topography of b-galactosidase expressing cells at the injection site corresponds to a limited spread of viral particles within the tissue and that anatomical boundaries such as large fiber tracts or the glia limitans prevent their diffusion.

Assays 5

Figure 5:
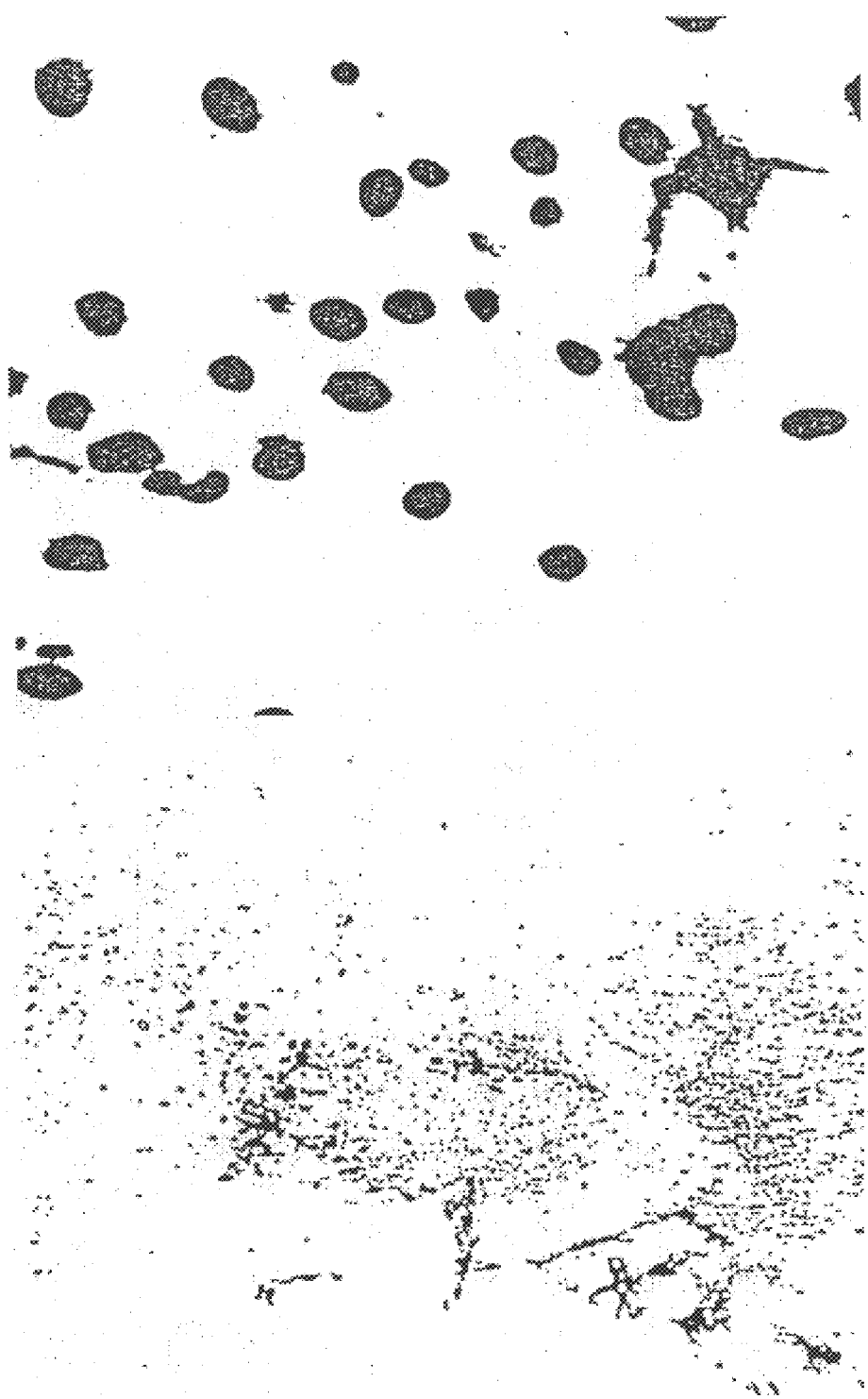
FIG. 5 shows labeling of nigral neurons after injection of adenovirus into the striatum.

In addition to cells labeled around the needle track, for which endocytosis of viral particles at the perikaryal level was likely, remote groups of neurons that send axonal projections to the area of injection were labeled, such as nigral neurons after injection into the striatum (FIG. 5).

Figure 6:
FIG. 6 shows b-gal histochemical staining following adenovirus injection into the striatum.

As a matter of fact FIG. 6 represents photomicrographs showing b-galactosidase histochemical staining following adenovirus injection into the striatum. Methods were the same as in Assay 4. a. Reaction product in cells at the periphery of the injection site. Reaction product is mostly in the nuclear-perinuclear region and intensity ranged from very faint (arrowheads) to strong, extending into neurons in the substantia nigra (SN) and in the ventral tegmental area (VTA) that have transported the viral vectors retrogradely from the striatum. x20.

The nuclear-perinuclear localization of the staining in nigral cells as well as the lack of a profuse staining in the nigro-striatal axonal pathway indicates that the viral particles rather than the enzyme was taken up by axonal terminals and transported retrogradely from the striatum to the substantia nigra. In contrast, no histochemical staining was observed in neurons that have axons crossing (but not ending in) the injection site, suggesting that viral particles cannot be endocytosed by axons of passage.

Assays 6

These above results underline the high level of neural cell infectability by the adenovirus. This has also been shown in the assays carried out as follows: Methods: The $3.3 \times 10^{10}$ pfu/ml suspension was either used directly or diluted using sterile saline before injection into the brain of 10 rats. Other methods are as described in Assays 4 except that sections were cut in the coronal plane.

Photomicrographs showing results obtained one week after injection into the thalamus of adenovirus suspension at different dilutions (sections counterstained with cresyl violet). a. Cytolytic effect observed after injection of 10 μl of a $3.3 \times 10^{10}$ pfu/ml suspension of viruses (total: $3.3 \times 10^8$ pfu). Tissue loss and gliotic areas (arrows reveal cell death induced by the viral injection. x20. (section not treated with X-gal). b.Staining after injection of a total of $3.3 \times 10^5$ pfu. Several thousand cells still expressed the gene, exhibiting mostly nuclear-perinuclear staining except for a few short neurites (arrowhead). There was no conspicuous cytolytic effect. x200. c. Staining after injection of $3.3 \times 10^3$ pfu. A few cells still expressed the gene (arrowheads) in a small area corresponding to the tip of the needle track. There was no apparent cytolytic effect. x400.

Considerable numbers of cells were infected after inoculation with high titer virus suspensions, but many cells were also infected when much lower titers were used. In rats injected with a 10 μl suspension titering $3.3 \times 10^7$ pfu/ml (a maximum of $3.3 \times 10^5$ infectious particles) several thousand neural cells still expressed the lacZ gene 8 days after inoculation (FIG. 6); injections as low as 3,300 pfu resulted in labeling of close to a hundred cells (FIG. 6). Intensity of labeling was another indication of the exquisite infectability of neural cells. When high titer virus suspensions were used (over $10^9$ pfu/ml) staining intensity was usually very strong in the center area of the injection site where cells are subjected to the highest viral particle concentration. In spite of the nls sequence added to b-galactosidase, labeling was so intense that it was not limited to nuclei of individual cells, but diffused to cytoplasm and processes (e.g. dendrites and axons of neurons) producing a complete "Golgi-like" staining of the cells (FIG. 6 and FIG. 5). In contrast, in most cells located at the periphery of the injection site and in retrogradely infected cells, only the nuclei were labeled (FIG. 5). Similarly, nuclear localization of the enzyme was the rule when lower titer virus suspensions were used (FIG. 6).

A single neural cell, in particular a neuron, can thus endocytose a massive amount of viral particles. This high infectability most likely explains the cytopathogenicity (characterized by neuronal death, gliosis, vascular ilammatory response and tissue loss) observed at the site of injection of high titer suspensions (FIG. 6). The absence of apparent cytopathogenicity of lower titer virus suspensions ($\leq 10^7$ pfu/ml) supports this hypothesis. Cytopathogenicity most likely relates, therefore, to the endocytosis of enormous numbers of viral particles by cells located close to the injection site.

Assays 7

Figure 7:
FIG. 7 shows expression of the lacZ gene by preserved neural cells 45 days after inoculation with adenovirus.

Adenovirus infection is clearly not systematically cytopathic, since well preserved neural cells expressing the lacZ gene were still observed 45 days after inoculation (FIG. 7). Nine rats were injected and sacrificed (n=3) every other week after injection. Surgical and histological methods as described in FIG. 4 except that sections were cut in the coronal plane. Photomicrographs showing b-galactosidase histochemical reaction product in a rat that was allowed to survive for forty-five days after adenovirus injection into the nucleus of the XIIth nerve (XII). A few cells still expressed the gene as demonstrated by nuclear-perinuclear histochemical staining. Among them were motoneurons as exemplified in the inset (counterstained with cresyl violet). A few axons also contained the enzyme (arrow). x40, inset x1000.

These results demonstrate that cells in the central nervous system, including neurons, can be successfully injected in large numbers by a replication-deficient adenovirus and consequently express a transferred foreign gene.

The impact on gene therapy is thus considerable. Although as mentioned above the invention aims at providing an alternative to the grafting in the patient whose cells carry a genetic defect of full neural cells containing the nucleic sequence aiming at compensating said genetic defect, particularly from an embryo, it should be understood that it may even further find a use in an improvement of such grafting techniques. Particularly the cells to be grafted could be "enriched" in or provided with the required nucleic sequence by in vitro transformation with an adenoviral vector containing that nucleic sequence, prior to be grafted according to the techniques already of use in cellular therapies. This improvement may be of particular significance in the case of primary cultures of neurons which do not undergo divisions.

Assays 8

This example discloses the construction of a recombinant defective adenoviral vector expressing the human tyrosine hydroxylase (hTH) cDNA : Ad LTR.hTH.

The adenovirus AdLTR.hTH was constructed by cotransfection of plasmid pLTR-IX-hTH with adenovirus deletion mutant Ad-dl1324 (Thimmappaya et al., Cell 31 (1982) 543) in 293 cells.

1. Construction of Plasmid pLTR-IX-hTH

The plasmid pLTR-IX-hTH was constructed by inserting the 1769 bp SalI-BstXI fragment of pSP6 HTH-1 (Horellou et al., J. Neurochem. 51 (1988) 652) containing the hTH-1 cDNA, in between the unique SalI and EcoRV sites of plasmid pLTR-IX, downstream with respect to the RSV LTR promoter. For that insertion, the BstXI restriction site was converted to blunt end with T4 DNA polymerase.

The plasmid pLTR-IX was obtained from plasmid pLTRβgal (Stratford-Perricaudet et al., J. Clin. Invest. 90 (1992) 626) by deletion of a ClaI-XhoI fragment bearing the βgal gene, digestion with klenow enzyme and ligation with T4 DNA ligase.

2. Construction of the Defective Recombinant Adenovirus AdLTR.hTH

The plasmid pLTR-IX-hTH and the adenovirus deletion mutant Ad-dl1324 were linearized with ClaI and co-transfected into cell line 293 in the presence of calcium phosphate, enabling homologous recombination. After recombination, the adenoviruses were selected, amplified on 293 cell line, and recovered by centrifugation on cesium chloride (Graham et al., Virology 52 (1973) 456).

Assays 9

This example discloses the in vitro and in vivo production of hTH using adenovirus AdLTR.hTH.

9.1. In vitro Production of hTH

Adenovirus recombinant vector Ad.LTR.hTH diclosed in assays 8 was used to infect 293 cell line. 24 to 48 hours after infection, cell pellets were recovered by centrifugation of the culture (1000 r/min, 5 min). The cell pellets were used for in vitro dosage of TH enzymatic activity (a), and in western analysis (b).

(a) Dosage of TH Enzymatic Activity

TH enzymatic activity was assayed using a method modified from Reinhard et al. (Life Sci. 39 (1986) 2185). Frozen cell pellets were sonicated for 30 s in ice cold 0.2%/100 mM Na HEPES, pH 6.99 and centrifuged (10,000 x g, 10 min). A fraction of the supernatant (10 $\mu$l) was used to assay TH activity by measuring the amount of $^3H_2O$ formed from L-[3,5-$^3$H]tyrosine during the incubation (10 min, 37° C.) in 100 $\mu$l of reaction medium (100 mM Na HEPES, pH 6.99, catalase (Sigma) 50 $\mu$g, 25 $\mu$M L-tyrosine (free-base, Sigma) and 0.2 $\mu$Ci L-[3,5-$^3$H]tyrosine (Amersham), 1 mM FeSO$_4$, 0.5 mM DL-6-methyl-5,6,7,8-tetrahydropterine, 5 mM dithiotreitol). The reaction was stopped by addition of 1 ml of 7.5% (w/v) charcoal (activated, Sigma) in 1 M HCl. The mixtures were then vortexed (3 s) and centrifuged (10,000 x g, 10 min). Aliquots (100 $\mu$l) of the supernatant were then transferred to scintillation vials containing 10 ml of scintillation cocktail (aqueous counting scintillant, Amersham) to measure the amount of $^3H_2O$ formed. To make L-tyrosine stock solution, L-[3,5-$^3$H]tyrosine was first speed-vacuum dried to eliminate the contaminating $^3H_2O$ before adding 500 $\mu$l of cold L-tyrosine 500 $\mu$M. Results are expressed in pmol of $^3H_2O$ formed by [$^3$H]tyrosine hydroxylation per hour per mg of protein. Protein quantitation was performed according to the method of Bradford et al.

This assay shows that 293 cells infected with Ad.LTR.hTH produce a TH activity capable of forming 5 $\mu$mol of DOPA/hour/mg protein, while uninfected 293 cells produce no TH activity.

(b) Western Analysis

Western analyses were performed by depositing protein extracts on SDS-Page electrophoresis gel (10% acrylamide), protein migration, and protein transfer onto nitrocellulose membrane. Nitrocellulose membranes were then incubated 48 hr at 4° C. with an anti-TH serum (Institut Jacques Boy) diluted 1:1000 in PBS containing 2% NS/0.05% Triton X-100. After 3 rinses, the membranes were incubated 2.5 h in swine-anti-rabbit IgG (Dakopatts, Denmark) diluted 1:50 in PBS/0.05% Triton X-100/2% NS. After another 3 rinses, they were incubated in rabbit peroxidase-antiperoxidase (Dakopatts) diluted 1:100 in PBS/0.05% Triton X-100. They were stained with 3,4-diarnnobenzidine (Sigma) and hydroxygen-peroxide and mounted for microscopic analysis.

In 293 cells infected with Ad.LTR.hTH, the anti-TH antibodies revealed a 62 kDa band corresponding to the MW of TH, while no band is detected in uninfected 293 cells.

9.2. In vivo Production of hTH

Young adult female Sprague-Dawley rats (ALAB, Stockholm, Sweden) were used in all experiments. 6-OHDA was injected stereotaxically into the right ascending mesostriatal DA pathway of 12 rats, under equithesin anaesthesia (3 ml/kg, i.p.).

Turning behavior was first monitored 10 days following the 6-OHDA lesion, after administration of apomorphine or d-amphetamine. Motor asymmetry was monitored in automated rotometer bowls (Ungerstedt and Arbuthnott, 1970) for 40 min following an injection of d-amphetamine (5 mg/kg, i.p.) or an injection of apomorphine hydrocloride (0.05 mg/kg, s.c. in the neck). 11 days following the 6-OHDA lesion, intrastriatal injections of recombinant adenovirus vector Ad.LTR.hTH (6 rats) or Ad RSVβGal (6 rats, as control) were performed in 3 different sites ($10^7$ pfu in 3 μl for each injection). Turning behavior (performed as disclosed before) and histological analysis were performed at days 20 and 27. The results obtained show that:

- Ad.LTR.hTH induced no toxic effect in rats (dopamine receptors were still functional)
- Ad.LTR.hTH injected rats produced TH protein, as demonstrated by immunological reactivity: The brains were immersed in 20% sucrose, 100 mM potassium phosphate (pHu7.4), for 1–2 days, and then sectioned at 40 μm thickness on a freezing microtome. Every third section was stained with cresyl violet and adjacent sections were processed for TH immunocytochemistry as described previously (Doucet et al., 1990). Briefly, after 3–4 rinses with phosphate buffered saline (PBS), free-floating sections were preincubated for 1 hr in 10% normal swine serum (NSS), 0.5% Triton X-100 in PBS, they were then incubated with an anti-TH serum (Institut Jacques Boy) diluted 1:1000 in PBS containing 5% NSS, 0.5% Triton X-100. After 3 rinses, the sections were incubated 2.5 hr in swine-anti-rabbit IgG (Dakopatts, Denmark) diluted 1:50 in PBS, 0.5% Triton X-100, 5% NSS. After another 3 rinses, they were incubated in rabbit peroxidase-anti-peroxidase (Dakopatts) diluted 1:100 in PBS, 0.5% Triton X-100, treated with 3,4-diaminobenzidine (Sigma) and hydroxygen-peroxide and mounted.
- Ad.LTR.hTH injected rats had a better turning behavior, showing a beneficial effect of Ad.LTR.hTH injection.

Assays 10

This example discloses the construction of a recombinant defective adenoviral vector expressing the murine ciliary neurotrophic factor: Ad LTR.CNTF.

The adenovirus AdLTR.CNTF was constructed by cotransfection of plasmid pLTR-IX-CNTF with adenovirus deletion mutant Ad-dl1324 (Thimmappaya et al., Cell 31 (1982) 543) in 293 cells.

1. Construction of Plasmid pLTR-IX-CNTF

The plasmid pLTR-IX-CNTF was constructed by inserting a HindIII-XbaI 1800 bp fragment of plasmid pRC.CMV.CNTF (Sendtner et al., Nature 358 (1992) 502) containing the murine CNTF gDNA (exons 1 and 2, intron 1) and the NGF leader sequence, in the unique EcoRV site of plasmid pLTR-IX, downstream with respect to the RSV LTR promoter. For that insertion, the HindIII-XbaI 1800 bp fragment was converted to blunt end with klenow DNA polymerase.

The plasmid pLTR-IX was obtained from plasmid pLTRβgal (Stratford-Perricaudet et al., J. Clin. Invest. 90 (1992) 626) by deletion of a ClaI-XhoI fragment bearing the βgal gene, digestion with klenow enzyme and ligation with T4 DNA ligase.

2. Construction of the Defective Recombinant Adenovirus AdLTR.CNTF

EagI-linearized pLTR-IX-CNTF DNA and ClaI-linearized adenovirus deletion mutant Ad-dl1324 were co-transfected into cell line 293 in the presence of calcium phosphate, enabling homologous recombination. After recombination, the adenoviruses were selected, amplified on 293 cell line, and recovered by centrifugation on cesium chloride (Graham et al., Virology 52 (1973) 456).

Assays 11

This example discloses the construction of a recombinant defective adenoviral vector containing the cDNA encoding the chain a of the hexosaminidase A: Ad LTR.HEXA. Genetic defects in the HEXA gene are responsible for Tay-Sachs lysosomal disease.

The adenovirus AdLTR.HEXA was constructed by cotransfection of plasmid pLTR-IX-HEXA with adenovirus deletion mutant Ad-dl1324 (Thimmappaya et al., Cell 31 (1982) 543) in 293 cells.

1. Construction of Plasmid pLTR-IX-HEXA

The plasmid pLTR-IX-HEXA was constructed by insuring a EcoRI 2000 bp fragment containing the cDNA encoding the chain a of the hexosaminidase A, obtained by screening of a lgt liver cDNA library (see also Proia et al., J. Biol. Chem. 262 (1987) 5677), in between the unique EcoRV site of plasmid pLTR-IX, downstream with respect to the RSV LTR promoter. For that insertion, the EcoRI 2000 bp fragment was converted to blunt end with T4 DNA polymerase.

The plasmid pLTR-IX was obtained from plasmid pLTRβgal (Stratford-Perricaudet et al., J. Clin. Invest. 90 (1992) 626) by deletion of a ClaI-XhoI fragment bearing the βgal gene, digestion with klenow enzyme and ligation with T4 DNA ligase.

2. Construction of the Defective Recombinant Adenovirus ADLTR.HEXA

AseI-linearized pLTR-IX-HEXA DNA and ClaI-linearized adenovirus deletion mutant Ad-dl1324 were cotransfected into cell line 293 in the presence of calcium phosphate, enabling homologous recombination. After recombination, the adenoviruses were selected, amplified on 293 cell line, and recovered by centrifugation on cesium chloride (Graham et al., Virology 52 (1973) 456).

Assays 12

This example discloses the construction of a recombinant defective adenoviral vector expressing the murine Nerve Growth Factor (hNGF) cDNA (PreproNGF): Ad LTR.NGF.

The adenovirus ADLTR.NGF was constructed by cotransfection of plasmid pLTR-IX-NGF with adenovirus deletion mutant Ad-dl1324 (Thimmappaya et al., Cell 31 (1982) 543) in 293 cells.

1. Construction of Plasmid pLTR-IX-NGF

The plasmid pLTR-IX-NGF was constructed by inserting a 1 kb EoRI-PstI fragment containing the prepro NGF cDNA into the corresponding sites of plasmid Bluescript (Stratagene). This cDNA was then isolated as a ClaI-BamHI fragment, converted to blunt end with Klenow enzyme, and inserted in between the unique ClaI and EcoRV sites of plasmid pLTR-IX, downstream with respect to the RSV LTR promoter.

The plasmid pLTR-IX was obtained from plasmid pLTRβgal (Stratford-Perricaudet et al., J. Clin. Invest. 90 (1992) 626) by deletion of a ClaI-XhoI fragment bearing the βgal gene, digestion with klenow enzyme and ligation with T4 DNA ligase.

2. Construction of the Defective Recombinant Adenovirus AdLTR.NGF

The plasmid pLTR-IX-NGF and the adenovirus deletion mutant Ad-dl1324 were linearized with ClaI and co-transfected into cell line 293 in the presence of calcium phosphate, enabling homologous recombination. After recombination, the adenoviruses were selected, amplified on 293 cell line, and recovered by centrifugation on cesium chloride (Graham et al., Virology 52 (1973) 456).

REFERENCES (1) Culver, W. C. et al., Science 256, 1550–1552 (1992)
(2) Johnson P. A., Miyanohara A., Levine F., Cahill T. & Friedman T., Virol. 66, 2952–2965 (1992)
(3) Fink K. D. et al., Hum. Gene Ther, 3, 11–19 (1992)
(4) Wolfe J. H., Deshmane S. L. & Fraser N. W., Nature genetics 1, 379–384 (1992)
(5) Stratford-Perricaudet L. D., Levrero M., Chase J. F., Perricaudet M. & Briand P., Hum. Gene Ther. 1, 241–256 (1990)
(6) Chroboezek J. et al, Virology 186, 280–285 (1992)
(7) Berkner K. L., Biotechniques 6, 612–629 (1988)
(8) Levrero M. et al, Gene 101, 195–202 (1991)
(9) L. D. Stratford-Perricaudet, I. Makeh, M. Perricaudet and P. Briand, J. Clin. Invest. 90, 626 (1992)
(10) J. R. Sanes, J. L. Rubenstein, J. F. Nicolas, Embo J. 5, 3133 (1986)
(11) L. D. Stratford-Perricaudet and M. Perricaudet, human gene transfer (Eds O. Cohen-Haguenauer, M. Boiron, J. Ubbey Eurotext Ltd, p.51 (1991)
(12) K. D. Mc Carthy and J. De Vellis, J. Cell Biol. 85, 890 (1980)
(13) A. P. Robinson, T. M. White and D. W. Mason, Immunology 57,239 (1986)
(14) C. E. Hayes and I. J. Goldstein, J. Biol. Chem. 249, 1904 (1974)

What is claimed is:

1. A method for expressing a gene in mammalian central nervous system cells, which method comprises
   modifying said cells to contain a replication-deficient recombinant adenovirus comprising said gene under the control of a promoter, wherein said gene encodes a polypeptide molecule functioning in said cells as a neurotransmitter-synthesizing enzyme, trophic factor, a growth factor, or a lysosomal enzyme, or wherein said gene is an antisense sequence, the transcription product of which blocks the expression in said cells of proteins responsible for neuropsychiatric disease, or of enzymes involved in the biosynthesis of said proteins or in the biosynthesis of glutamate; and
   wherein the gene is expressed in said modified cells.

2. The method of claim 1 wherein said cells are contained in a mammal.

3. The method of claim 2 wherein said modifying comprises stereotactical injection at a site within the brain.

4. The method of claim 3 wherein said site is the striatum, the thalamus, the hippocampus, or the substantia nigra.

5. The method of claim 1, wherein said cells are brain cells or spinal cord cells.

6. The method of claim 5 wherein said cells are neural, glial or ependymal cells.

7. The method of claim 1, wherein said adenovirus comprises all of the sequences of the adenoviral genome which are required for encapsidation of the adenovirus in cells infected by said adenovirus.

8. The method of claim 7, wherein said adenovirus is devoid of the E1A and E1B regions of the adenovirus genome.

9. The method of claim 8, wherein said adenovirus is devoid of the E3 regions of the adenovirus genome.

10. The method of claim 1, wherein said promoter is exogenous with respect to the adenoviral genome.

11. The method of claim 10, wherein said promoter is a neuronal, glial, or ependymal promoter.

12. The method of claim 1, wherein said nucleotide sequence encodes a neurotransmitter-synthesizing enzyme.

13. The method of claim 12, wherein said neurotransmitter-synthesizing enzyme is tyrosine hydroxylase, choline acetyl transferase, tryptophan hydroxylase, enolase G, aldoase C or glutamic acid decarboxylase.

14. The method of claim 13, wherein the enzyme is tyrosine hydroxylase.

15. The method of claim 1, wherein the nucleotide sequence encodes a trophic factor.

16. The method of claim 15, wherein the trophic factor is a neurotrophic factor.

17. The method of claim 16, wherein the neurotrophic factor is CNTF, GMF, NT3, NT5 or BDNF.

18. The method of claim 17, wherein the neurotrophic factor is NT3.

19. The method of claim 1, wherein the nucleotide sequence encodes a growth factor.

20. The method of claim 19, wherein said growth factor is IGF, aFGF, bFGF, or nerve growth factor.

21. The method of claim 1, wherein the nucleotide sequence encodes a lysosomal enzyme.

22. The method of claim 21, wherein the lysosomal enzyme is hexosaminidase, arylsulfatase, glucocerebrosidase, 3-glucocerebrosidase or HGPRT.

23. A recombinantly modified nonhuman mammal having central nervous system cells infected with a replication-deficient adenovirus vector comprising a gene under the control of promoter, wherein said gene has been expressed in the nervous system cells of said mammal, and said gene encodes a polypeptide molecule functioning in said cells as a neurotransmitter-synthesizing enzyme, a trophic factor, a neurotrophic factor, a growth factor, nerve growth factor or a lysosomal enzyme, or wherein said gene is an antisense sequence, the transcription product of which blocks the expression of proteins responsible for neuropsychiatric disease, of enzymes involved in the biosynthesis of said proteins or in the biosynthesis of glutamate.

24. The mammal of claim 23, wherein said adenovirus comprises all of the sequences of the adenoviral genome which are required for encapsidation of the adenovirus in cells infected by said adenovirus.

25. The mammal of claim 24, wherein said adenovirus is devoid of the E1A and E1B regions of the adenovirus genome.

26. The mammal of claim 25, wherein said adenovirus is devoid of the E3 regions of the adenovirus genome.

27. The mammal of claim 23, wherein said promoter is exogenous with respect to the adenovirus genome.

28. The mammal of claim 27, wherein said promoter is a neuronal, glial, or ependymal promoter.

29. The mammal of claim 23, wherein said nucleotide sequence encodes a neurotransmitter-synthesizing enzyme.

30. The mammal of claim 29, wherein said neurotransmitter-synthesizing enzyme is tyrosine hydroxylase, choline acetyl transferase, tryptophan hydroxylase, enolase G, aldoase C or glutamic acid decarboxylase.

31. The mammal of claim 30, wherein the enzyme is tyrosine hydroxylase.

32. The mammal of claim 23, wherein the nucleotide sequence encodes a trophic factor.

33. The mammal of claim 32, wherein the trophic factor is a neurotrophic factor.

34. The mammal of claim 33, wherein the neurotrophic factor is CNTF, GMF, NT3, NT5 or BDNF.

35. The mammal of claim 34, wherein the neurotrophic factor is NT3.

36. The mammal of claim 23, wherein the nucleotide sequence encodes a growth factor.

37. The mammal of claim 36, wherein said growth factor is IGF, aFGF, bFGF, or nerve growth factor.

38. The mammal of claim 23, wherein the nucleotide sequence encodes a lysosomal enzyme.

39. The mammal of claim 38, wherein the lysosomal enzyme is hexosaminidase, arylsulfatase, glucocerebrosidase, 3-glucocerebrosidase or HGPRT.

40. A method for treating Parkinson's Disease which method comprises stereotactically administering to the brain of a mammal suffering from Parkinson's Disease a pharmaceutical composition comprising a replication-defective adenovirus which infects central nervous system cells of said mammal and expressing a nucleotide sequence, contained in said adenovirus, which nucleotide sequence encodes a neurotransmitter-synthesizing enzyme whereby said subject is treated for Parkinson's disease.

41. The method of claim 40 wherein the neurotransmitter-synthesizing enzyme is tyrosine hydroxylase.

42. A method for expressing a gene in mammalian central nervous system cells, comprising modifying said cells to contain a replication-deficient recombinant adenovirus comprising said gene under the control of a promoter, wherein said gene is an antisense sequence, the transcription product of which blocks the expression in said cells of b-amyloid, b-amyloid precursor or TAU; and wherein the gene is expressed in said modified cells.

43. A recombinantly modified nonhuman mammal having central nervous system cells infected with a replication-deficient adenovirus vector comprising a gene under the control of promoter, wherein said gene has been expressed in the nervous system cells of said mammal, and said gene is an antisense sequence, the transcription product of which blocks the expression of b-amyloid, b-amyloid precursor or TAU.

44. An ex vivo population of central nervous system cells comprising a replication-defective adenovirus, wherein said adenovirus comprises a nucleotide sequence operably linked to a promoter, wherein said nucleotide sequence encodes a polypeptide molecule functioning in said cells as a neurotransmitter-synthesizing enzyme, a trophic factor, a growth factor, or a lysosomal enzyme.

45. The population of central nervous system cells of claim 44, wherein said cells are neural, glial, or ependymal cells.

46. The population of central nervous system cells of claim 45, wherein said cells are neurons or astrocytes.

47. The population of central nervous system cells of claim 46, wherein said cells are astrocytes.

48. The population of central nervous system cells of claim 44, wherein said adenovirus comprises an encapsidation sequence.

49. The population of central nervous system cells of claim 48, wherein said adenovirus is devoid of E1A and E1B regions of the adenovirus genome.

50. The population of central nervous system cells of claim 49, wherein said adenovirus is devoid of the E3 region of the adenovirus genome.

51. The population of central nervous system cells of claim 44, wherein said promoter is exogenous with respect to the adenovirus genome.

52. The population of central nervous system cells of claim 51, wherein the promoter is a neuronal, glial or ependymal promoter.

53. The population of central nervous system cells of claim 44, wherein said nucleotide sequence encodes a neurotransmitter-synthesizing enzyme.

54. The population of central nervous system cells of claim 53, wherein said neurotransmitter-synthesizing enzyme is selected from the group consisting of tyrosine hydroxylase, choline acetyl transferase, tryptophan hydroxylase, enolase G, aldolase C and glutamic acid decarboxylase.

55. The population of central nervous system cells of claim 54, wherein the enzyme is tyrosine hydroxylase.

56. The population of central nervous system cells of claim 44, wherein the nucleotide sequence encodes a trophic factor.

57. The population of central nervous system cells of claim 56, wherein the trophic factor is a neurotrophic factor.

58. The population of central nervous system cells of claim 57, wherein the neurotrophic factor is selected from the group consisting of CNTF, GMF, NT3, NT5 and BDNF.

59. The population of central nervous system cells of claim 58, wherein the neurotrophic factor is NT3.

60. The population of central nervous system cells of claim 44, wherein the nucleotide encodes a growth sequence factor.

61. The population of central nervous system cells of claim 60, wherein said growth factor is IGF, aFGF, bFGF or nerve growth factor.

62. The population of central nervous system cells of claim 44, wherein the nucleotide sequence encodes a lysosomal enzyme.

63. The population of central nervous system cells of claim 62, wherein the lysosomal enzyme is selected from the group consisting of hexosaminidase, arylsulfatase, glucocerebrosidase, 3-glucocerebrosidase and HGPRT.

64. The population of central nervous system cells of claim 44, wherein said cells are in a form suitable for grafting into a host.

65. A process for producing a protein or polypeptide comprising culturing central nervous system cells comprising a replication defective adenovirus, wherein said adenovirus comprises a nucleotide sequence encoding said protein or polypeptide and operably linked to a promoter, wherein said protein or polypeptide is a neurotransmitter-synthesizing enzyme, a trophic factor, a growth factor, or a lysosomal enzyme.

66. The process of claim 65, wherein said nucleotide sequence encodes a neurotransmitter-synthesizing enzyme.

67. The process of claim 66, wherein said neurotransmitter-synthesizing enzyme is selected from the group consisting of tyrosine hydroxylase, choline acetyl transferase, tryptophan hydroxylase, enolase G, aldolase C and glutamic acid decarboxylase.

68. The process of claim 67, wherein the enzyme is tyrosine hydroxylase.

69. The process of claim 65, wherein the nucleotide sequence encodes a trophic factor.

70. The process of claim 69, wherein the trophic factor is a neurotrophic factor.

71. The process of claim 70, wherein the neurotrophic factor is selected from the groups consisting of CNTF, GMF, NT3, NT5 and BDNF.

72. The process of claim 71, wherein the neurotrophic factor is NT3.

73. The process of claim 65, wherein the nucleotide sequence encodes a growth factor.

74. The process of claim 73, wherein said growth factor is IGF, aFGF, bFGF or nerve growth factor.

75. The process of claim 65, wherein the nucleotide sequence encodes a lysosomal enzyme.

76. The process of claim 75, wherein the lysosomal enzyme is selected from the group consisting of hexosaminidase, arylsulfatase, glucocerebrosidase, 3-glucocerebrosidase and HGPRT.

77. A population of central nervous system cells disposed in a nonhuman animal comprising a replication-defective adenovirus, wherein said adenovirus comprises a nucleotide sequence operably linked to a promoter, wherein said nucleotide sequence encodes a polypeptide molecule functioning in said cells as a neurotransmitter-synthesizing enzyme, a trophic factor, a growth factor, or a lysosomal enzyme.

78. The population of central nervous system cells of claim 77, wherein said cells are neural, glial, or ependymal cells.

79. The population of central nervous system cells of claim 78, wherein said cells are neurons or astrocytes.

80. The population of central nervous system cells of claim 77, wherein said adenovirus comprises an encapsidation sequence.

81. The population of central nervous system cells of claim 80, wherein said adenovirus is devoid of E1A and E1B regions of the adenovirus genome.

82. The population of central nervous system cells of claim 81, wherein said adenovirus is devoid of the E3 region of the adenovirus genome.

83. The population of central nervous system cells of claim 77, wherein said promoter is exogenous with respect to the adenovirus genome.

84. The population of central nervous system cells of claim 83, wherein the promoter is a neuronal, glial or ependymal promoter.

85. The population of central nervous system cells of claim 77, wherein said nucleotide sequence encodes a neurotransmitter-synthesizing enzyme.

86. The population of central nervous system cells of claim 85, wherein said neurotransmitter-synthesizing enzyme is selected from the group consisting of tyrosine hydroxylase, choline acetyl transferase, tryptophan hydroxylase, enolase G, aldolase C and glutamic acid decarboxylase.

87. The population of central nervous system cells of claim 86, wherein the enzyme is tyrosine hydroxylase.

88. The population of central nervous system cells of claim 77, wherein the nucleotide sequence encodes a trophic factor.

89. The population of central nervous system cells of claim 88, wherein the tropic factor is a neurotrophic factor.

90. The population of central nervous system cells of claim 89, wherein the neurotrophic factor is selected from the group consisting of CNTF, GMF, NT3, NT5 and BDNF.

91. The population of central nervous system cells of claim 77, wherein the nucleotide sequence encodes a growth factor.

92. The population of central nervous system cells of claim 77, wherein the nucleotide sequence encodes a lysosomal enzyme.

93. An isolated population of human central nervous system cells comprising a replication-defective adenovirus, wherein said adenovirus comprises a nucleotide sequence operably linked to promoter, wherein said nucleotide sequence encodes a polypeptide molecule functioning in said cells as a neurotransmitter-synthesizing enzyme, a trophic factor, a growth factor, or a lysosomal enzyme.

94. The population of central nervous system cells of claim 93, wherein said cells are neural, glial, or ependymal cells.

95. The population of central nervous system cells of claim 94, wherein said cells are neurons or astrocytes.

96. The population of central nervous system cells of claim 93, wherein said adenovirus comprises an encapsidation sequence.

97. The population of central nervous system cells of claim 96, wherein said adenovirus is devoid of EIA and EIB regions of the adenovirus genome.

98. The population of central nervous system cells of claim 97, wherein said adenovirus is devoid of the E3 region of the adenovirus genome.

99. The population of central nervous system cells of claim 93, wherein said promoter is exogenous with respect to the adenovirus genome.

100. The population of central nervous system cells of claim 99, wherein the promoter is a neuronal, glial or ependymal promoter.

101. The population of central nervous system cells of claim 93, wherein said nucleotide sequence encodes a neurotransmitter-synthesizing enzyme.

102. The population of central nervous system cells of claim 101, wherein said neurotransmitter-synthesizing enzyme is selected from the group consisting of tyrosine hydroxylase, choline acetyl transferase, tryptophan hydroxylase, enolase G, aldolase C and glutamic acid decarboxylase.

103. The population of central nervous system cells of claim 102, wherein the enzyme is tyrosine hydroxylase.

104. The population of central nervous system cells of claim 93, wherein the nucleotide sequence encodes a trophic factor.

105. The population of central nervous system cells of claim 104, wherein the tropic factor is a neurotrophic factor.

106. The population of central nervous system cells of claim 105, wherein the neurotrophic factor is selected from the group consisting of CNTF, GMF, NT3, NT5 and BDNF.

107. The population of central nervous system cells of claim 93, wherein the nucleotide sequence encodes a growth factor.

108. The population of central nervous system cells of claim 93, wherein the nucleotide sequence encodes a lysosomal enzyme.

* * * * *

UNITED STATES PATENT AND TRADEMARK OFFICE
CERTIFICATE OF CORRECTION

PATENT NO. : 6,756,523 B1 Page 1 of 1
APPLICATION NO. : 08/460478
DATED : June 29, 2004
INVENTOR(S) : Kahn et al.

It is certified that error appears in the above-identified patent and that said Letters Patent is hereby corrected as shown below:

Title page, item (73), add an additional Assignee:

"Institut National de la Sante et de la Recherche Medicale".

Signed and Sealed this

Thirtieth Day of December, 2008

JON W. DUDAS
*Director of the United States Patent and Trademark Office*